United States Patent
Allred

(10) Patent No.: US 9,993,230 B2
(45) Date of Patent: Jun. 12, 2018

(54) SHAVE BIOPSY DEVICES AND RELATED METHODS

(71) Applicant: Seton Healthcare Family, Austin, TX (US)

(72) Inventor: James Allred, Austin, TX (US)

(73) Assignee: SETON HEALTHCARE FAMILY, Austin, TX (US)

( * ) Notice: Subject to any disclaimer, the term of this patent is extended or adjusted under 35 U.S.C. 154(b) by 303 days.

(21) Appl. No.: 14/661,188

(22) Filed: Mar. 18, 2015

(65) Prior Publication Data

US 2016/0051236 A1  Feb. 25, 2016

Related U.S. Application Data

(60) Provisional application No. 62/040,013, filed on Aug. 21, 2014.

(51) Int. Cl.
*A61B 5/00* (2006.01)
*A61B 10/02* (2006.01)

(52) U.S. Cl.
CPC ................ *A61B 10/0233* (2013.01)

(58) Field of Classification Search
CPC ............ A61B 10/02; A61B 10/0233
USPC ................................. 600/564, 570
See application file for complete search history.

(56) References Cited

U.S. PATENT DOCUMENTS

| 951,456 A | 3/1910 | Saxton | 30/49 |
|---|---|---|---|
| 1,174,932 A | 3/1916 | Grenier | 30/51 |
| 1,893,524 A | 1/1933 | Shanley | 606/161 |
| 1,934,151 A | 11/1933 | Slama et al. | 30/346.58 |
| 1,974,568 A | 9/1934 | Grotenhuis | 30/34.05 |
| 2,035,110 A | 3/1936 | Becker et al. | 30/346.59 |
| 2,041,778 A | 5/1936 | Peters | 30/346.56 |
| 2,361,921 A | 11/1944 | Albert | 30/50 |
| 2,421,205 A | 5/1947 | Kingsley | 30/49 |
| 2,453,198 A | 11/1948 | Corbett | 30/312 |
| 3,688,407 A | 9/1972 | Paquette | 433/144 |
| 4,038,986 A | 8/1977 | Mahler | 606/132 |
| 4,221,222 A | 9/1980 | Detsch | 606/132 |
| 4,438,767 A | 3/1984 | Nelson | 606/131 |
| 4,516,320 A | 5/1985 | Peleckis | 30/49 |
| 4,542,742 A | 9/1985 | Winkelman et al. | 606/167 |
| 4,651,734 A | 3/1987 | Doss et al. | 606/50 |

(Continued)

FOREIGN PATENT DOCUMENTS

| WO | WO 98/018604 | 5/1998 |
|---|---|---|
| WO | WO 2005/112790 | 12/2005 |
| WO | WO 2010/014716 | 2/2010 |

*Primary Examiner* — Max Hindenburg
(74) *Attorney, Agent, or Firm* — Norton Rose Fulbright US LLP

(57) ABSTRACT

This disclosure includes shave biopsy devices having an elongated body with a proximal surface extending between first and second ends that are configured to be grasped by a user's fingers and a blade coupled to the body, where the body is configured to be curved such that the proximal surface is concave. In some devices, at least a portion of the body has a substantially fixed curvature. Some devices include a depth gauge disposed on at least one of the blade and proximal surface of the body, the depth gauge configured to indicate slicing depth of the blade when the body is curved to at least one predetermined curvature.

14 Claims, 3 Drawing Sheets

(56) References Cited

U.S. PATENT DOCUMENTS

| | | | |
|---|---|---|---|
| 4,690,139 A * | 9/1987 | Rosenberg | A61B 17/322 |
| | | | 606/132 |
| 4,782,590 A | 11/1988 | Pope | 30/50 |
| 4,887,356 A | 12/1989 | Rudd | 30/30 |
| 4,893,641 A | 1/1990 | Strickland | 132/200 |
| 4,912,846 A | 4/1990 | Yu | 30/81 |
| 4,916,816 A | 4/1990 | Richman | 30/339 |
| 4,943,295 A | 7/1990 | Hartlaub et al. | 606/131 |
| 5,555,892 A | 9/1996 | Tipton | 600/564 |
| 5,624,451 A | 4/1997 | Segal | 606/131 |
| 5,628,759 A | 5/1997 | McCool et al. | 606/167 |
| 5,674,234 A | 10/1997 | McCool et al. | 606/167 |
| 5,979,056 A | 11/1999 | Andrews | 30/49 |
| 5,983,499 A | 11/1999 | Andrews | 30/29.5 |
| 6,018,877 A | 2/2000 | Greene | 30/526 |
| 6,112,421 A | 9/2000 | Greene | 30/526 |
| 6,266,888 B1 | 7/2001 | Zowaski | 30/527 |
| 6,505,403 B1 | 1/2003 | Andrews | 30/29.5 |
| 7,481,775 B2 * | 1/2009 | Weikel, Jr. | A61B 10/0275 |
| | | | 600/564 |
| 7,513,902 B2 | 4/2009 | Banbury et al. | 606/131 |
| 7,806,907 B2 | 10/2010 | Banbury et al. | 606/167 |
| 8,192,435 B2 | 6/2012 | Bleich et al. | 606/79 |
| 8,782,911 B1 * | 7/2014 | Greene | B26B 21/52 |
| | | | 30/298 |
| 8,931,379 B2 * | 1/2015 | Allyn | A61B 10/02 |
| | | | 30/51 |
| 2011/0130678 A1 | 6/2011 | Williamson | 600/564 |

\* cited by examiner

SHAVE BIOPSY DEVICES AND RELATED METHODS

CROSS-REFERENCE TO RELATED APPLICATIONS

This application claims priority to U.S. Provisional Patent Application No. 62/040,013 filed Aug. 21, 2014, which is incorporated by reference in its entirety.

BACKGROUND

1. Field of Invention

The present invention relates generally to tissue biopsies, and more specifically, but not by way of limitation, to shave biopsy devices configured to indicate a slicing depth (e.g., in real-time during a biopsy).

2. Description of Related Art

Shave biopsy is one technique that can be used obtain a tissue sample (e.g., to determine if a skin lesion is benign or is potentially harmful to a patient). During a shave biopsy, at least a portion of a skin lesion is typically removed (e.g., is shaved off), such that the removed portion can be tested for cancer and/or the like. Shave biopsies are generally quick, cost-effective, and relatively straightforward.

When performing a shave biopsy, depth (e.g., slicing depth) can be critical. For example, if a biopsy is too deep, the risk for bleeding, infections, damage to underlying structures, scarring, slow healing, and/or the like can be increased. On the other hand, if a biopsy is too shallow, adequate staging of the biopsied lesion (e.g., if malignant) and/or future treatment can be complicated.

To illustrate, if a melanoma is deeper than 1 millimeter (mm), a sentinel lymph node biopsy may be desirable (e.g., using a wide local excision with a relatively large margin); however, if a melanoma is shallower than 1 mm, a lymph node biopsy may not be necessary. Thus, it may be desirable that shave biopsies be taken at least 1 mm deep because, for example, if a shave biopsy is too shallow and the lesion is transected, it may not be possible to determine if a large excision or lymph node biopsy is necessary (e.g., because it may not be possible to accurately determine the depth of the lesion).

Examples of cutting and/or biopsy devices are disclosed in U.S. Patents (1) U.S. Pat. No. 2,453,198; and (2) U.S. Pat. No. 5,555,892.

SUMMARY

Some embodiments of the present shave biopsy devices are configured, through a depth gauge disposed on a blade and/or a proximal surface of the device, to indicate (e.g., in real-time, during a biopsy) slicing depth of the device, such as, for example, to facilitate excising a sufficient portion of a skin lesion without putting the patient at risk for excess scarring. Some embodiments are configured, through an elongated body curved to at least one predetermined curvature, to facilitate accurate slicing depth and/or to indicate accurate indications from a depth gauge. In some embodiments, the curvature of the body is fixed and/or is fixable, such as, for example, via an elongated body that is at least partially rigid, a supporting member configured to maintain a curvature of the body, and/or the like.

Some embodiments of the present shave biopsy devices comprise an elongated body having a proximal surface extending between first and second ends that are configured to be grasped by a user's fingers, at least a portion of the body having a substantially fixed curvature such that the proximal surface is concave, and a blade coupled to the body. Some embodiments comprise a depth gauge disposed on at least one of the blade and the proximal surface of the body, the depth gauge configured to indicate slicing depth of the blade.

Some embodiments of the present shave biopsy devices comprise an elongated body having a proximal surface extending between first and second ends that are configured to be grasped by a user's fingers, the body configured to be curved such that the proximal surface is concave, a blade coupled to the body, and a depth gauge disposed on at least one of the blade and the proximal surface of the body, the depth gauge configured to indicate slicing depth of the blade when the body is curved to at least one predetermined curvature. In some embodiments, at least a portion of the body has a substantially fixed curvature. In some embodiments, the curvature of the body is substantially symmetrical about a plane that bisects the shave biopsy device between the first and second ends. In some embodiments, the body is substantially rigid.

In some embodiments, the depth gauge is configured to measure slicing depth relative to the center of the blade. In some embodiments, the depth gauge comprises a plurality of markings. In some embodiments, the markings comprise ink deposited on at least one of the blade and the proximal surface of the body. In some embodiments, the markings are raised. In some embodiments, a distance measured along the blade or the proximal surface body the body between adjacent markings decreases with distance from the center of the blade.

Some embodiments comprise a supporting member configured to extend between the first and second ends of the body to resist separation of the first and second ends. In some embodiments, the body is biased toward a non-curved configuration and the supporting member is configured to resist the bias and maintain curvature of the body.

In some embodiments, the supporting member is configured such that a first portion of the supporting member extends beyond the first end of the body to define a first gripping member, and a second portion of the supporting member extends beyond the second end of the body to define a second gripping member. In some embodiments, the supporting member defines a plurality of slots, each configured to receive a portion of the body. In some embodiments, at least a portion of the supporting member is unitary with at least a portion of the body. In some embodiments, the supporting member comprises a transparent material. In some embodiments, the supporting member comprises a length gauge configured to indicate dimensions of a tissue to be biopsied. In some embodiments, the supporting member comprises a wire. In some embodiments, the supporting member comprises a rod.

In some embodiments, the body includes gripping surfaces at the first and second ends. In some embodiments, the body comprises plastic. In some embodiments the blade comprises stainless steel.

Some embodiments of the present methods for performing a shave biopsy comprise slicing with a blade of a shave biopsy device, the shave biopsy device having an elongated body with a concave proximal surface extending between first and second ends, where the slicing is at a depth indicated by a depth gauge disposed on the proximal surface. Some embodiments comprise curving the body before slicing. In some embodiments, the body is curved to a predetermined curvature. Some embodiments comprise coupling a supporting member to the body to resist separation of the first and second ends.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments are described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DETAILED DESCRIPTION OF ILLUSTRATIVE EMBODIMENTS

Figure 1A:
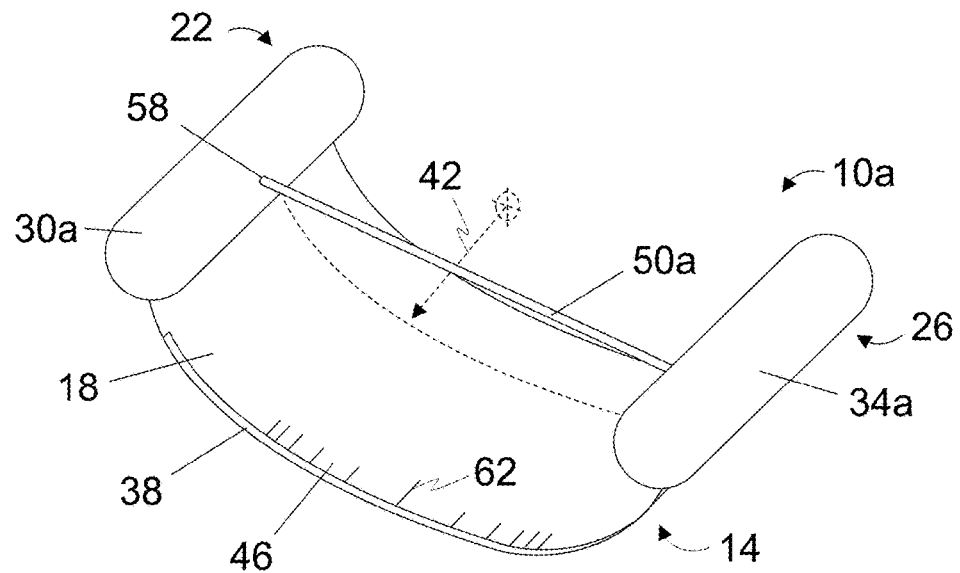
FIG. 1A is a perspective view of a first embodiment of the present shave biopsy devices, shown in a curved configuration.

Referring now to the drawings, and more particularly to FIGS. 1A, 1B, 2A, and 2B, shown therein and designated by the reference numeral 10a is a first embodiment of the present shave biopsy devices. In the embodiment shown, device 10a comprises an elongated body 14 having a proximal surface 18 extending between a first end 22 and a second end 26. In this embodiment, the first and second ends are configured to be grasped by a user's (e.g., a clinician's) fingers. For example, first end 22 and second end 26 can each define or otherwise include a gripping member 30a and 34a, respectively (e.g., each comprising a gripping surface and/or otherwise configured to facilitate grasping of device 10a between fingers of a user's hand). In this embodiment, body 14 comprises plastic; however, in other embodiments, the body can comprise any suitable material, such as, for example, aluminum, stainless steel, and/or the like.

In the embodiment shown, device 10a comprises a blade 38 coupled to body 14. As shown, blade 38 is coupled to and runs along a majority of an edge of body 14 (e.g., to form a cutting edge for performing a shave biopsy). In this embodiment, device 10a comprises one blade 38, however, in other embodiments, device 10a can comprise more than one blade (e.g., two blades disposed on opposing edges of body 14). In the depicted embodiment, body 14 is molded around blade 38 (e.g., blade 38 is non-removable). However, in other embodiments, the present devices can be configured such that blade 38 is replaceable. In some embodiments, such as those in which body 14 comprises steel, blade 38 can be unitary with body 14 (e.g., formed from the same piece of material).

Figure 1B:
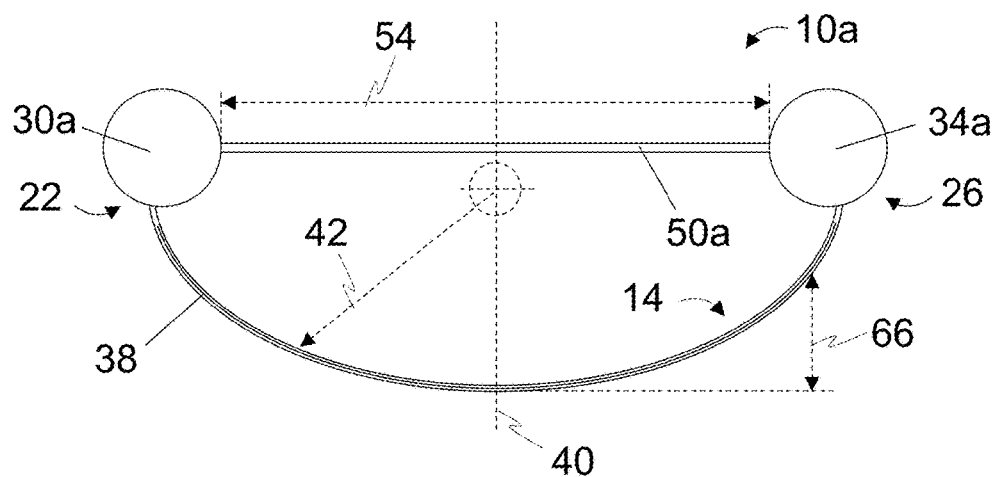
FIG. 1B is a front view of the device of FIG. 1A.
Figure 2A:
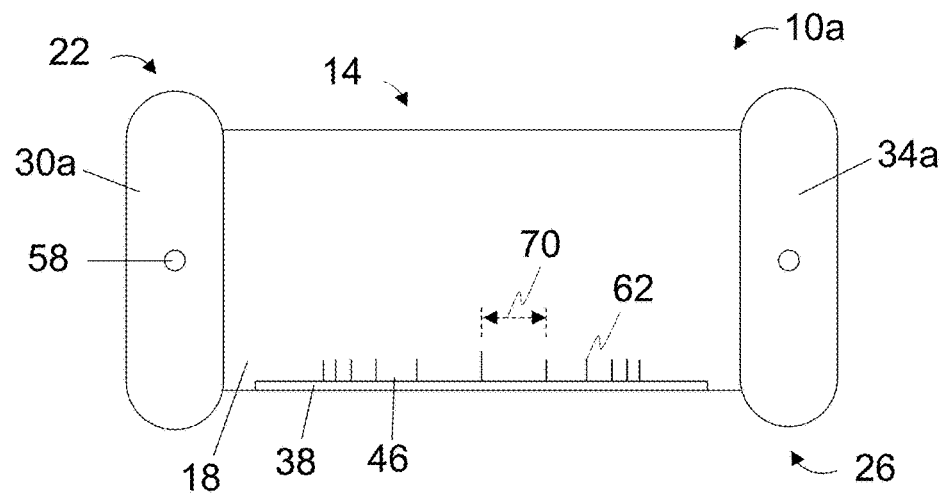
FIG. 2A is a top view of the device of FIG. 1A, shown in an uncurved configuration.
Figure 2B:
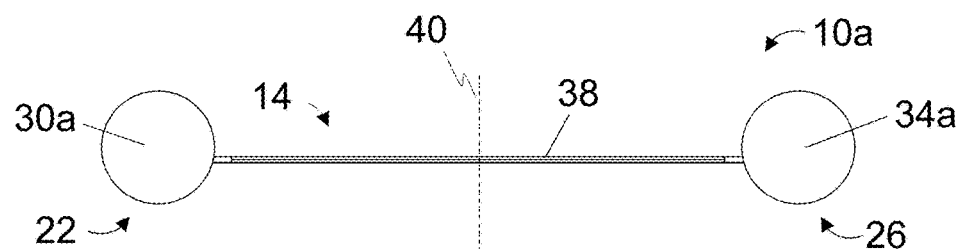
FIG. 2B is a front view of the device of FIG. 2A.

In the embodiment shown, body 14 is configured to be curved such that proximal surface 18 is concave relative to a user and convex relative to a patient from whom a biopsy is obtained. For example, in this embodiment, body 14 (e.g., and/or blade 38) is resilient, and griping members 30a and 34a are offset from body 14 (e.g., longitudinally when device 10a is uncurved, as shown in FIG. 2B) such that application of a lateral force to the gripping members tends to induce curvature 42 to body 14 (e.g., as shown in FIG. 1B). As shown, body 14 and/or blade 38 are configured to be curved to a generally smoothly curved and generally elliptical curvature; however, in other embodiments, through configuration of body 14 and/or blade 38 (e.g., thickness, length, width, material properties, and/or the like, which may vary along a direction from first end 22 to second end 26), the present devices can be configured to be curved to any suitable curvature, such as, for example, generally triangular, circular, and/or the like. In this embodiment, body 14 (e.g., whether curved as in FIG. 1B or not curved as in FIG. 2B) is substantially symmetrical about a plane 40 that bisects device 10a between the first and second ends.

In the embodiment shown, at least a portion of device 10a is configured to have a fixed or a fixable curvature 42 (e.g., to facilitate accurate slicing depth indications from depth gauge 46, described below).

For example, in this embodiment, device 10a comprises a supporting member 50a (e.g., a wire, spring, rod, and/or the like) configured to extend between first end 22 and second end 26 (e.g., substantially without contacting other portions of body 14) to resist separation of the first and second ends.

Particularly, in the depicted embodiment, body 14 and/or blade 38 is resilient and is biased towards an uncurved configuration (FIGS. 2A and 2B) and supporting member 50a is configured to resist the bias and maintain a curvature (e.g., which may be predetermined, prior to performing a biopsy).

In this embodiment, through at least configuration of supporting member 50a, curvature 42 can be varied. For example, as a length 54 of supporting member 50a is increased, curvature 42 will generally decrease; and, as length 54 of supporting member 50a is decreased, curvature 42 will generally increase. In this embodiment, supporting member 50a is configured to be received by gripping members 30a and 34a of first and second ends 22 and 26 (e.g., within and/or through holes or openings 58). However, in other embodiments, such as those in which the curvature of body 14 is fixed, supporting member 50a can be unitary with body 14.

In some embodiments, at least a portion of the present devices (e.g., up to and including all of body 14 and/or blade 38) can be substantially rigid in a curved configuration (FIGS. 1A and 1B), such that the portion has a substantially fixed curvature. In some embodiments, at least a portion of the present devices can be flexible, yet not resilient, such that a user can bend and/or otherwise form the device to the desired curvature before performing a biopsy. In these and other embodiments, supporting member 50a may be omitted.

In the embodiment shown, device 10a comprises a depth gauge 46 disposed on at least one of blade 38 and proximal surface 18 of body 14 (e.g., body 14, as shown). For example, in this embodiment, depth gauge 46 comprises a plurality of markings 62 (e.g., ink markings, deposited on blade 38 and/or body 14). In some embodiments, the markings are raised or depressed (e.g., by etching) relative to proximal surface 18 of body 14 and/or a proximal surface of blade 38 (e.g., to enhance visibility of the markings).

Depth gauge 46 can be configured to indicate slicing depth of blade 38 when the body is curved to at least one predetermined curvature (as described above). In this embodiment, depth gauge 46 is configured to measure slicing depth (e.g., 66) of blade 38 relative to the center of the blade (e.g., in this embodiment, the most distal point of the blade). For example, as shown, a distance 70, measured along blade 38 or proximal surface 18, between adjacent markings decreases with distance from the center of the blade (e.g., to account for a pre-determined curvature 42 of device 10a). For example, as a clinician biopsies a lesion, a portion of the lesion can move across proximal surface 18, where depth gauge 46 can be used to indicate the depth of the slice (e.g., in real time).

In some embodiments, device 10a can be configured to be curved to more than one fixed and/or fixable predetermined curvature 42. For one example, some embodiments of the present devices can comprise a plurality of supporting members of varying (e.g., and/or adjustable) lengths 54, such that the devices can be curved to a plurality of predetermined curvatures. In such embodiments, depth gauge 46 can be configured to measure a slicing depth at any one or more of the plurality of curvatures. For example, depth gauge 46 can comprise multiple marking sets, which may be distinguishable from one another (e.g., through differing sizes, lengths, thicknesses, colors, and/or the like amongst the marking sets), where each marking set corresponds to one of the plurality of predetermined curvatures.

As another example, an additional depth gauge can be disposed on an opposite side of body 14 and/or blade 38 from depth gauge 46 (e.g., disposed on a distal surface of body 14 and/or blade 38). In these embodiments, the device can be curvable to at least two predetermined curvatures (one in which proximal surface is concave (e.g., as shown in FIGS. 1A and 1B), and one in which proximal surface is convex) (e.g., and the opposing depth gauges can each be configured to correspond to a different one of the two curvatures, which need not possess the same shape and/or magnitude).

Via at least depth gauge 46, a clinician can accurately assess the depth at which a biopsy is being performed (e.g., to ensure a biopsy of at least 1 mm deep). Thus, through device 10a, incorrectly transecting a lesion too shallowly can be avoided, and the ability to determine the actual depth of the lesion can be preserved. The present device can thus be particularly useful for clinicians learning to perform shave biopsies, or for clinicians performing shave biopsies in delicate areas where avoiding scar formation is particularly important (e.g., a patient's face). Thus, device 10a is configured to perform shave biopsies in a safe and precise fashion.

Figure 3:
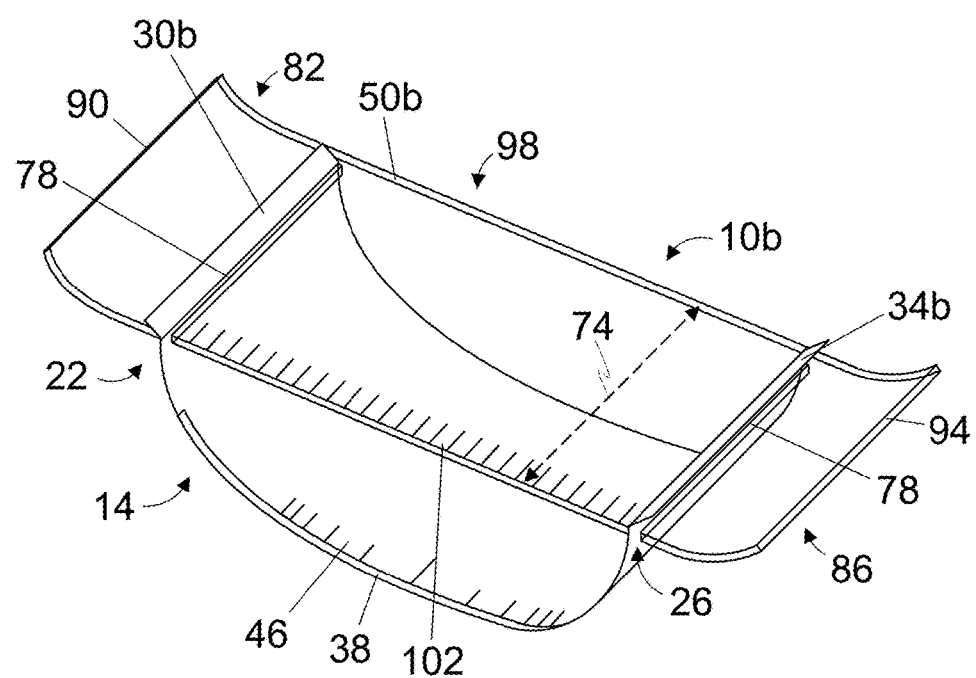
FIG. 3 is a perspective view of a second embodiment of the present shave biopsy devices, shown in a curved configuration.

Referring now to FIG. 3, shown therein and designated by the reference numeral 10b is a second embodiment of the present shave biopsy devices. Device 10b is substantially similar to device 10a, with the primary exceptions described below. Similarly to as described above for supporting member 50a of device 10a, in the embodiment shown, supporting member 50b of device 10b is configured to extend between first end 22 and second end 26 of body 14 to resist separation of the first and second ends. In this embodiment, supporting member 50b has a width 74 configured to extend along a majority of (e.g., up to and including all of) a corresponding width of body 14, when the supporting member is coupled to the body. In at least this way, supporting member 50b may be configured to increase a stiffness of device 10b (e.g., facilitating accurate biopsies, accurate measurements from depth gauge 46, and/or the like).

In the depicted embodiment, supporting member 50b defines a plurality of slots 78, each configured to receive a portion of body 14. In the embodiment shown, slots 78 are each configured to receive a portion of body 14 located between first end 22 of the body and second end 26 of the body, and the first and second ends (e.g., and/or respective gripping surfaces 30b and 34b) are configured (e.g., sized, placed, and/or the like) such that the first and second ends (e.g., and/or the respective gripping surfaces) are each physically prevented from longitudinally passing through a corresponding one of the slots. In at least this way, slots 78 may cooperate with first end 22 and second end 26 (e.g., and/or respective gripping surfaces 30b and 34b) to maintain body 14 of device 10b at a predetermined curvature. In embodiments where body 14 is biased toward a non-curved configuration (e.g., 10b), bias of the body may induce a frictional force between the body and sidewall(s) of slots 78 of supporting member 50b that resists separation of the body and the supporting member. In this embodiment, supporting member 50b comprises two (2) slots 78; however, in other embodiments, supporting members (e.g., 50b) may comprise any suitable number of slots (e.g., 78) (e.g., and pairs of such slots may each correspond to a respective predetermined curvature of a body 14 associated with the supporting member). Of course, slots 78 are provided only by way of example, as, in other embodiments, supporting members (e.g., 50b) may be coupled to respective bodies (e.g., 14) in any suitable fashion, such as, for example, through adhesive(s), fastener(s), other interlocking features, and/or the like. In yet other embodiments, at least a portion of (e.g., up to and including all of) a supporting member (e.g., 50*b*) may be unitary and/or integrally formed with at least a portion of (e.g., up to and including all of) a body (e.g., 14).

In the depicted embodiment, supporting member 50*b* is configured such that, when the supporting member is coupled to body 14, a first portion 82 of the supporting member extends (e.g., laterally) beyond first end 22 of the body to define a first gripping member 90, and a second portion 86 of the supporting member extends (e.g., laterally) beyond second end 26 of the body to define a second gripping member 94. In the embodiment shown, portions 82 and 86 of supporting member 50*b* each extend longitudinally (e.g., and proximally) away from a generally planar portion 98 of the supporting member (e.g., such that surface(s) of each of gripping members 90 and 94 are angularly disposed relative to generally planar portion 98). In these ways and others, supporting member 50*b* may function as a handle, facilitating, for example, increased control over device 10*b* when performing a biopsy.

In the embodiment shown, supporting member 50*b* comprises a transparent and/or translucent material (e.g., a plastic, acrylic, polycarbonate, and/or the like). In this way, when supporting member 50*b* is coupled to body 14, a user may view portions of body 14, blade 38, depth gauge 46, and/or the like that would otherwise be obstructed by the supporting member (e.g., while performing a biopsy). In this embodiment, supporting member 50*b* comprises a length gauge (e.g., ruler) 102 configured to indicate dimensions of a tissue to be biopsied. Thus, for example, a user may measure a measure dimensions of a lesion to be biopsied using length gauge 102 (e.g., prior to performing a biopsy of the lesion).

Some embodiments of the present methods for performing a shave biopsy comprise slicing with a blade (e.g., 38) of a shave biopsy device (e.g., 10*a*, 10*b*, and/or the like), the shave biopsy device having an elongated body (e.g., 14) with a concave proximal surface (e.g., 18) extending between first and second ends (e.g., 22 and 26, respectively), where the slicing is at a depth (e.g., 66) indicated by a depth gauge (e.g., 46) disposed on the proximal surface. Some methods comprise curving the body (e.g., to a curvature 42) before slicing. In some methods, the body is curved to a predetermined curvature. Some methods comprise coupling a supporting member (e.g., 50*a*, 50*b*, and/or the like) to the body to resist separation of the first and second ends.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A shave biopsy device comprising:
   an elongated body having a proximal surface extending between first and second ends that are configured to be grasped by a user's fingers, at least a portion of the body having a substantially fixed curvature such that the proximal surface is concave;
   a blade coupled to the body; and
   a depth gauge disposed on at least one of the blade and the proximal surface of the body, the depth gauge configured to indicate slicing depth of the blade;
   where:
      the depth gauge is configured to measure slicing depth relative to the center of the blade;
      the depth gauge comprises a plurality of markings; and
      a distance measured along the blade or the proximal surface of the body between adjacent markings decreases with distance from the center of the blade.

2. The shave biopsy device of claim 1, where the body is substantially rigid.

3. The shave biopsy device of claim 1, comprising a supporting member configured to extend between the first and second ends of the body to resist separation of the first and second ends.

4. The shave biopsy device of claim 3, where the supporting member is configured such that:
   a first portion of the supporting member extends beyond the first end of the body to define a first gripping member; and
   a second portion of the supporting member extends beyond the second end of the body to define a second gripping member.

5. The shave biopsy device of claim 3, where the supporting member comprises a transparent material.

6. The shave biopsy device of claim 3, where the supporting member comprises a length gauge configured to indicate dimensions of a tissue to be biopsied.

7. The shave biopsy device of claim 3, where the supporting member defines a plurality of slots, each configured to receive a portion of the body.

8. The shave biopsy device of claim 3, where the supporting member comprises a rod.

9. The shave biopsy device of claim 3, where the body is biased toward a non-curved configuration and the supporting member is configured to resist the bias and maintain curvature of the body.

10. The shave biopsy device of claim 1, where the body includes gripping surfaces at the first and second ends.

11. A method for performing a shave biopsy comprising:
    slicing with a blade of a shave biopsy device of claim 1;
    where the slicing is at a depth indicated by the depth gauge.

12. The method of claim 11, comprising curving the body before slicing.

13. The method of claim 12, where the body is curved to a predetermined curvature.

14. The method of claim 11, comprising coupling a supporting member to the body to resist separation of the first and second ends.

\* \* \* \* \*